(12) United States Patent
Deshmukh et al.

(10) Patent No.: US 7,553,843 B2
(45) Date of Patent: Jun. 30, 2009

(54) PROCESS FOR THE PREPARATION OF PURIFIED CRYSTALLINE CCI-779

(75) Inventors: Subodh S. Deshmukh, White Plains, NY (US); Clifford William Coughlin, Plattsburgh, NY (US); Chunhao Zhang, La Salle (CA); Adam P. Michaud, Lawrenceville, NJ (US); Lynn M. Phelan, Lake Hiawatha, NJ (US); Wei Tong, Suffern, NY (US)

(73) Assignee: Wyeth, Madison, NJ (US)

( * ) Notice: Subject to any disclaimer, the term of this patent is extended or adjusted under 35 U.S.C. 154(b) by 358 days.

(21) Appl. No.: 11/634,774

(22) Filed: Dec. 6, 2006

(65) Prior Publication Data

US 2007/0129395 A1    Jun. 7, 2007

Related U.S. Application Data

(60) Provisional application No. 60/748,006, filed on Dec. 7, 2005.

(51) Int. Cl.
  *C07D 498/12*  (2006.01)
  *A61K 31/453*  (2006.01)
  *A61P 35/00*   (2006.01)

(52) U.S. Cl. ..................................... 514/291; 540/456
(58) Field of Classification Search ................ 540/456; 514/291
  See application file for complete search history.

(56) References Cited

U.S. PATENT DOCUMENTS

| 5,362,718 | A  | 11/1994 | Skotnicki et al. |
| 5,385,908 | A  | 1/1995  | Nelson et al. |
| 5,385,909 | A  | 1/1995  | Nelson et al. |
| 6,277,983 | B1 | 8/2001  | Shaw et al. |
| 6,432,973 | B1 | 8/2002  | Zhu et al. |
| 7,074,804 | B2 | 7/2006  | Zhu et al. |
| 7,153,957 | B2 | 12/2006 | Chew et al. |
| 2005/0049271 | A1 | 3/2005 | Benjamin et al. |
| 2005/0234087 | A1 | 10/2005 | Gu et al. |
| 2005/0234234 | A1 | 10/2005 | Gu et al. |
| 2006/0036091 | A1 | 2/2006 | Cai et al. |
| 2006/0135549 | A1 | 6/2006 | Graziani et al. |
| 2006/0135550 | A1 | 6/2006 | Graziani et al. |
| 2006/0178392 | A1 | 8/2006 | Deshmukh et al. |
| 2006/0199253 | A1 | 9/2006 | Shaw et al. |
| 2006/0199834 | A1 | 9/2006 | Zhu |

FOREIGN PATENT DOCUMENTS

WO   WO-2005/016935   2/2005

OTHER PUBLICATIONS

International Search Report dated Apr. 16, 2007 issued in International Patent Application No. PCT/US2006/046444.

*Primary Examiner*—Bruck Kifle
(74) *Attorney, Agent, or Firm*—David A. Rubin, Esq.; Howson & Howson LLP

(57) ABSTRACT

The present invention provides purified crystalline CCI-779 and processes for preparing the same.

28 Claims, 2 Drawing Sheets

PROCESS FOR THE PREPARATION OF PURIFIED CRYSTALLINE CCI-779

CROSS-REFERENCE TO RELATED APPLICATIONS

This application claims the benefit under 35 USC 119(e) of U.S. Provisional Patent Application No. 60/748,006, filed Dec. 7, 2005.

BACKGROUND OF THE INVENTION

The present invention provides purified crystalline CCI-779 and processes for preparing same.

Rapamycin 42-ester with 3-hydroxy-2-(hydroxymethyl)-2-methylpropionic acid (CCI-779) is an ester of rapamycin which has demonstrated significant inhibitory effects on tumor growth in both in vitro and in vivo models. CCI-779 has been demonstrated to be effective in multiple applications, including as an anticancer agent for treating central nervous system cancer, leukemia, breast cancer, prostate cancer, melanoma, gliomas, and glioblastoma.

CCI-779 may delay the time to progression of tumors or time to tumor recurrence which is more typical of cytostatic rather than cytotoxic agents. CCI-779 is considered to have a mechanism of action that is similar to that of sirolimus. CCI-779 binds to and forms a complex with the cytoplasmic protein FKBP, which inhibits an enzyme, mTOR (mammalian target of rapamycin, also known as FKBP12-rapamycin associated protein (FRAP)). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. The mechanism of action of CCI-779 that results in the G1-S phase block is novel for an anticancer drug.

In vitro, CCI-779 has been shown to inhibit the growth of a number of histologically diverse tumor cells. Central nervous system (CNS) cancer, leukemia (T-cell), breast cancer, prostate cancer, and melanoma lines were among the most sensitive to CCI-779. The compound arrested cells in the G1 phase of the cell cycle.

In vivo studies in nude mice have demonstrated that CCI-779 has activity against human tumor xenografts of diverse histological types. Gliomas were particularly sensitive to CCI-779 and the compound was active in an orthotopic glioma model in nude mice. Growth factor (platelet-derived)-induced stimulation of a human glioblastoma cell line in vitro was markedly suppressed by CCI-779. The growth of several human pancreatic tumors in nude mice as well as one of two breast cancer lines studied in vivo also was inhibited by CCI-779.

CCI-779 has been purified by several recrystallization processes, which produce a form of CCI-779 that contains unacceptable amounts of impurities. Other routes to more purified CCI-779 include chromatography purifications, which provide a purer form of CCI-779. These chromatography purifications, however, cannot be scaled up to produce any appreciable amounts of purified CCI-779, nor would doing so be financially beneficially.

Alternate processes for preparing purified forms of CCI-779, especially processes performed on a larger scale, are needed.

SUMMARY OF THE INVENTION

Figure 1:
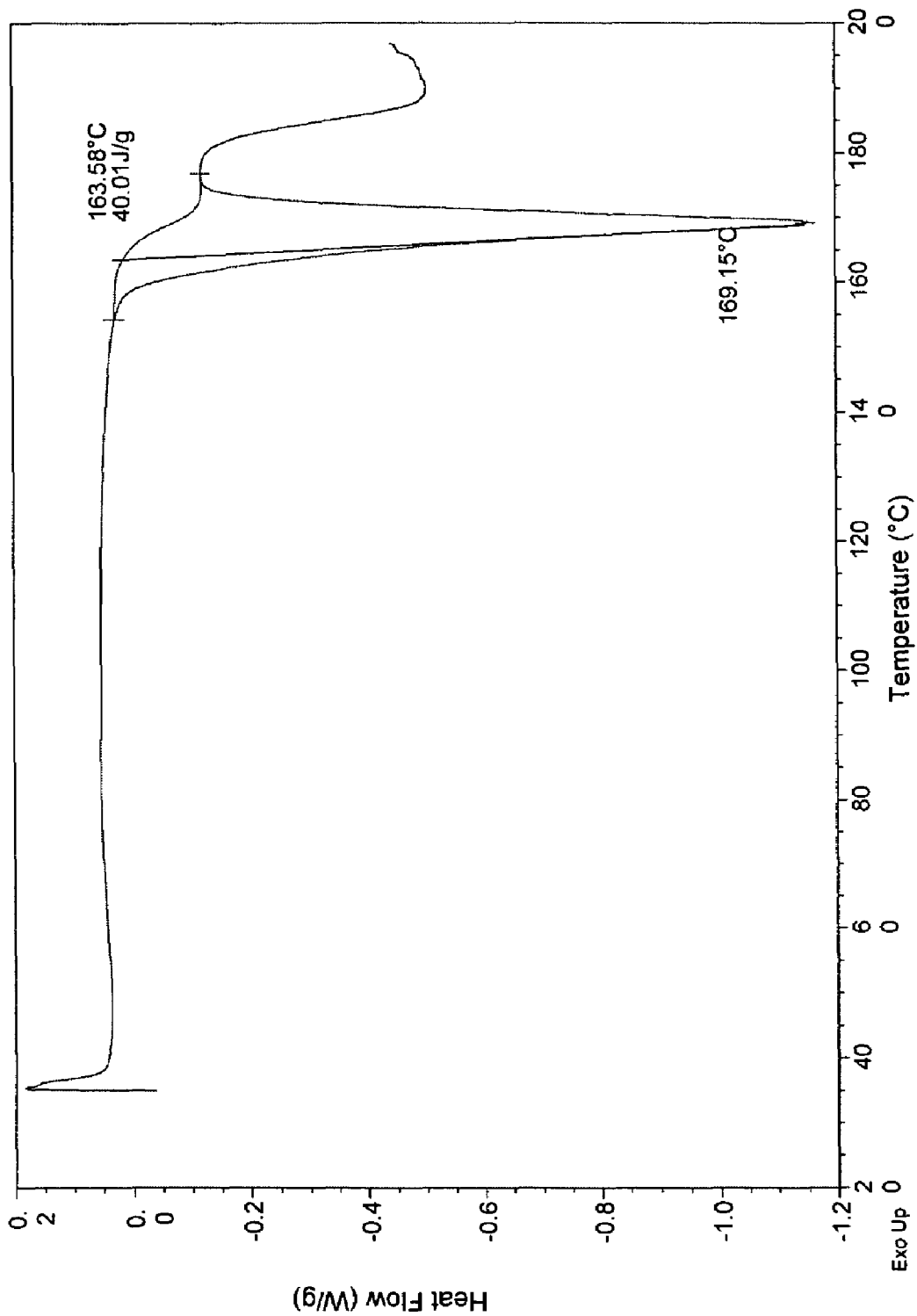
FIG. 1 provides the differential scanning calorimetry thermogram of one representative sample of purified crystalline CCI-779 prepared according to the present invention.
Figure 2:
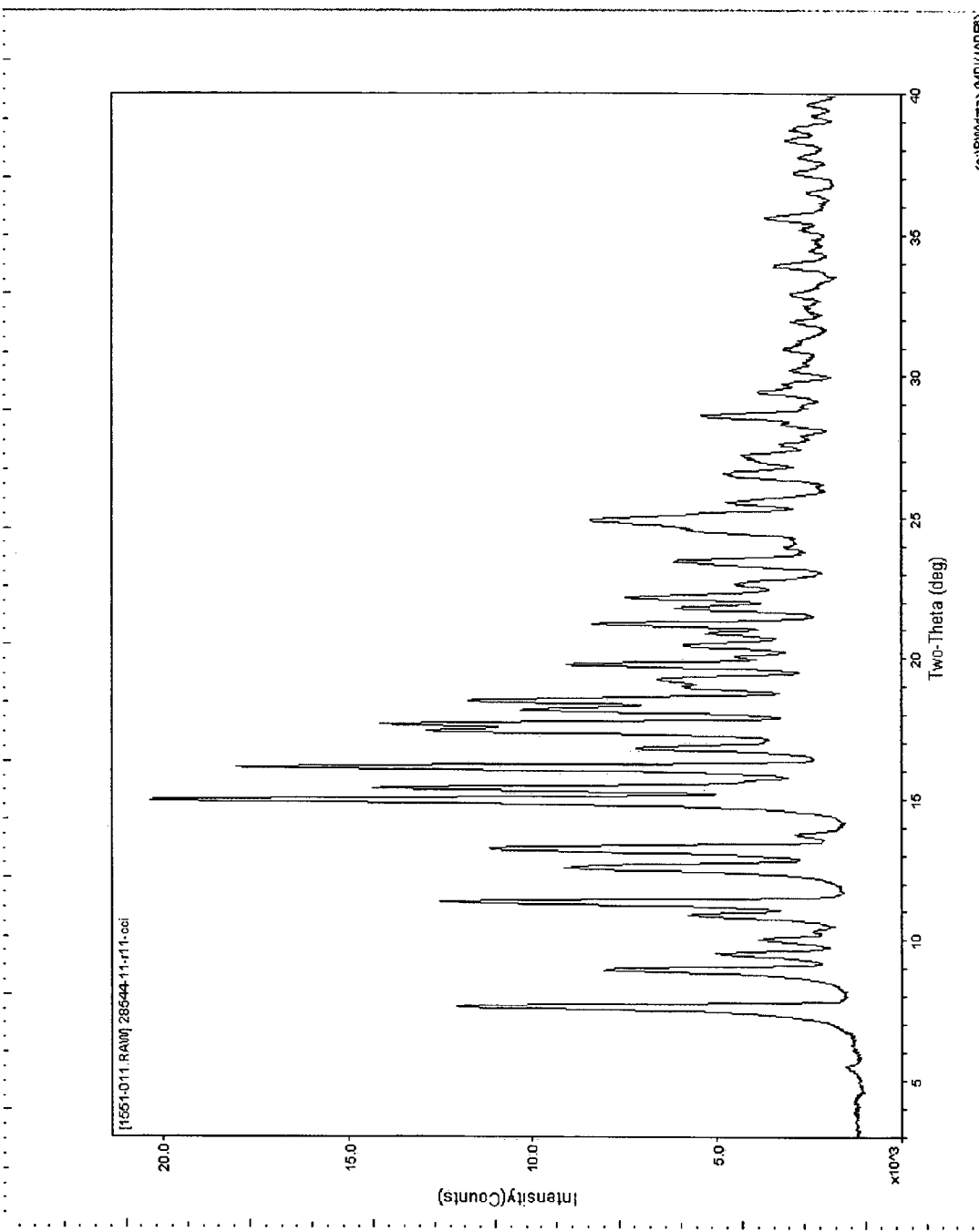
FIG. 2 provides the X-ray diffraction pattern of one representative sample of purified crystalline CCI-779 prepared according to the present invention.

In one aspect, the present invention provides purified crystalline CCI-779.

In a further aspect, the present invention provides purified crystalline CCI-779 which process does not include chromatography.

In another aspect, the present invention provides purified crystalline CCI-779 which purification thereof does not include chromatography.

In yet a further aspect, the present invention provides a process for preparing purified crystalline CCI-779.

In still another aspect, the present invention provides a process for purifying CCI-779.

In a further aspect, the present invention provides a method for monitoring crystallization and/or purification of CCI-779.

Other aspects and advantages of the present invention are described further in the following detailed description of the preferred embodiments thereof.

DETAILED DESCRIPTION OF THE INVENTION

The present invention provides a process for preparing purified crystalline CCI-779 with good crystallinity. This process also can be performed successfully on a large scale, without adversely affecting the purity of the CCI-779 product and in good yields.

The good crystallinity of the purified CCI-779 contributes to the improved stability of the purified CCI-779 and longer shelf life, and contains less oxidative impurities. In one embodiment, the purified crystalline CCI-779 of the present invention degrades less than about 3%, less than about 2%, or less than about 1% over a period of about 1 month. Desirably, the purified crystalline CCI-779 retains greater than 97% strength over a period of about 3 months, and more desirably about 6 months at about 5° C. as measured by high performance liquid chromatography (HPLC), among other techniques. The strength is similarly maintained at elevated temperatures up to about 70° C., desirably up to about 51° C., more desirably temperatures up to about 25° C. and greater relative humidities up to about 60%, and most desirably temperatures at about 5° C., or combinations thereof. In one embodiment, the purified crystallized CCI-779 prepared according to the present invention maintains its stability at a temperature of about 25° C. and relative humidity of about 60% for up to about 3 months, and more desirably up to about 6 months.

The purified crystalline CCI-779 prepared according to the present invention typically contains less than 0.6% wt/wt of oxidative impurities. Desirably, the purified CCI-779 also contains less than 0.1% wt/wt of phenylboronic acid and less than about 0.3% wt/wt of acetone. The term "oxidative impurity" as used herein refers to impurities that are produced due to degradation of residual phenylboronic acid in the solid sample of purified crystalline CCI-779.

The purified crystalline CCI-779 typically has a differential scanning calorimetry (DSC) thermogram having an endotherm peak greater than about 165° C. Desirably, the endotherm peak is at about 165° C., 166° C., 167° C., 168° C., 169° C., or 170° C. Similarly, the X-ray diffraction (XRD) peak pattern of the purified crystalline CCI-779 typically contains peaks at 2θ with an area intensity of greater than about 25%±a 2θ of 0.2. For example, the XRD pattern of the purified crystalline CCI-779 typically contains peaks at 2θ of about 7.7, 9.0, 11.4, 12.6, 13.3, 15.0, 15.4, 16.2, 66.5, 34.8, 43.7, 31.4, and 58.

In one embodiment, the present invention provides purified crystalline CCI-779 having a DSC thermogram having an endotherm peak greater than about 165° C.; and an XRD peak pattern having peaks at 2θ of about 7.7, 9.0, 11.4, 12.6, 13.3, 15.0, 15.4, 16.2, 66.5, 34.8, 43.7, 31.4, and 58.

In another embodiment, the present invention provides purified crystalline CCI-779 which comprises less than about 0.6% wt/wt of phenylboronic acid.

A. Process for Preparing Purified Crystalline CCI-779

Also provided by the present invention is a process for preparing purified crystalline CCI-779. The process of the invention advantageously provides a route to purified crystalline CCI-779 without the use of chromatography for the purification. The present process also provides purified crystalline CCI-779 on a large scale.

The first step in the process of the invention includes dissolving unpurified CCI-779 in a first solvent. Desirably, the CCI-779 is highly soluble in the first solvent. Typically, the first solvent is a ketone. In one embodiment, the first solvent is acetone, methyl ethyl ketone, diethyl ketone, or methyl isobutyl ketone. In a further embodiment, the first solvent is acetone. In another embodiment, the first solvent is methyl ethyl ketone, among others. However, one of skill in the art would readily be able to select a suitable first solvent for use in the present invention by using the teachings of the present invention. Once dissolved in the first solvent, the solution is typically filtered to remove any solid particles.

The term "unpurified CCI-779" or "crude CCI-779" as used herein refers to a less pure and/or crystalline form of CCI-779. There are a variety of methods for preparing unpurified or crude CCI-779 and include U.S. Pat. Nos. 5,362,718 and 6,277,983, which are hereby incorporated by reference. Alternatively, CCI-779 can be purchased commercially (e.g., Wyeth). The unpurified or crude CCI-779 can be non-micronized or micronized as described in US Patent Application Publication No. US-2005-0152983-A1, which is hereby incorporated by reference.

The first solvent is then removed from the filtered solution, typically using reduced pressures, optionally in the presence of heat. One of skill in the art would readily be able to use adjust the conditions for removing the first solvent or would be able to use other methods for removing the first solvent.

Once the first solvent is removed, CCI-779 is obtained, typically as a foam, solid, or combination thereof. Typically, trace amounts of the first solvent remains in the residual CCI-779 foam, solid, or combination thereof. However, the CCI-779 obtained as the foam, solid, or combination thereof can lack any first solvent therein. In one embodiment, the CCI-779 is amorphous. In another embodiment, the CCI-779 is partially crystalline.

The CCI-779 obtained after removal of the first solvent is then dissolved in a second solvent. Desirably, the CCI-779 is less soluble in the second solvent than in the first solvent. The CCI-779 is dissolved in a minimal amount of the second solvent. The term "minimal amount" refers to the smallest volume of second solvent that permits dissolution of the majority of the CCI-779. Alternatively, the CCI-779 is first dissolved in greater amounts of the second solvent and then the volume of the solution reduced by using techniques known to those of skill in the art including reduced pressures. One of skill in the art would also be able to readily recognize when the volume of the solution has been reduced to acceptable amounts.

Suitably, the solubility of the CCI-779 in the second solvent is determined by visual inspection. Typically, the solution containing the CCI-779 and second solvent is visually inspected to ensure that most of the CCI-779 dissolved. One of skill in the art would readily be able to utilize techniques to effect further dissolution of the CCI-779 in the second solvent. Alternatively, the solubility of the solid CCI-779 is determined by an analytical device such as a turbidity probe or a focused beam reflectance measurement (FBRM® probe). In one embodiment, the second solvent is an ether. In another embodiment, the second solvent has a polarity similar to the polarity of diethyl ether. In a further embodiment, the second solvent is diethyl ether. The solution is also optionally filtered after dissolution of the CCI-779 in the second solvent.

Once dissolved, the content of the first solvent, typically acetone, in the solution of the second solvent/CCI-779 is measured. Desirably, the content of the first solvent is less than about 4 vol %, and more desirably the content of the acetone is less than about 3 vol %. Typically, the content of the first solvent in the second solvent is measured using HPLC. If the content of the first solvent in the solution exceeds 4 vol %, the second solvent is removed using reduced pressures, optionally in the presence of heat, to re-form solid CCI-779. The solid CCI-779 is treated with a second aliquot of the second solvent and the content of the first solvent again measured. These steps are repeated until the content of the first solvent in a solution of the CCI-779/second solvent is less than 4 vol %. Typically, the second solvent is removed at least once before the acceptable first solvent content is reached.

In addition to measuring the acetone content, the present invention also provides measuring the nucleation point of purified CCI-779 prior to crystallization of the same in the second solvent. The term "nucleation" as used herein refers to the spontaneous formation of crystalline CCI-779 from a supersaturated solution of CCI-779 in the second solvent, such as ether. The "nucleation point", i.e., the point at which nucleation begins, is typically measured by focused beam reflectance measurement (FBRM®), of which there are a variety of FBRM® instruments available in the art and useful in the present invention and include the Lasentec® D 600L or S400 FBRM® systems. The FBRM® instrument is useful to ensure high crystallinity and purity of the CCI-779 crystalline product. Typically, the nucleation point is achieved when the chord count of the particles of CCI-779 formed in the solution is greater than 1500 chords/second for 1 to 5 μm size particles of the purified crystalline CCI-779.

The term "chord" as used herein refers to a straight-line path across the cross-section of a particle and is an averaged dimension of the length of the particle. One of skill in the art may also describe a chord simplistically as a measure of the width of the particle. Desirably, the term "chord" as used herein refers to a CCI-779 crystalline particle. The term "chord count" as used herein refers to the number of particles of a certain chord length or size fraction.

The nucleation point can be adjusted by varying the nucleation hold time during measurement with the FBRM® instrument until the desired chord count is achieved. If a scavenging agent is utilized in the present invention, the "nucleation hold time" refers to the period of time that the CCI-779 in the second solvent is maintained before the scavenging agent is added. If a scavenging agent is omitted from the process of the invention, the "nucleation hold time" refers to the period of time that the CCI-779 in the second solvent is maintained before the anti-solvent is added. The nucleation point is desirably determined by monitoring the FBRM® signal as described above.

Once the desired content of the first solvent in the second solvent and nucleation point has been achieved, a scavenging agent is optionally added to remove residual phenylboronic acid. The inventors have found that residual phenylboronic acid can degrade in solid samples of CCI-779, thereby resulting in the formation of oxidative impurities, which can lead to the breakdown of CCI-779, particularly during storage. Desirably, the scavenging agent is pentanediol and is added to the solution containing the second solvent and the CCI-779.

Crystallization of purified CCI-779 can begin at various stages during purification and can vary from one run to another. Typically, crystallization begins after addition of the second solvent. Desirably, crystallization begins (i) during measurement of the first solvent in the second solvent, (ii) during measurement of the nucleation point, or a combination thereof.

After addition of the optional scavenging agent, an anti-solvent is added to obtain solid purified crystalline CCI-779 or purified crystalline CCI-779 that had not yet crystallized in the solution. The term "anti-solvent" as used herein refers to a solvent that minimally or does not dissolve the purified crystalline CCI-779. If a scavenging agent is utilized in the process, the anti-solvent is added to the solution containing the second solvent, CCI-779, and scavenging agent. If a scavenging agent is not utilized in the process, the anti-solvent is added to the solution containing the second solvent and CCI-779. In one embodiment, the anti-solvent is a hydrocarbon and is desirably a straight chain or branched saturated hydrocarbon. Typically, the hydrocarbon has about 6 to about 10 carbon atoms. In one embodiment, the hydrocarbon is heptane, 2-methyl pentane, n-hexane, and combinations thereof, among others. In another embodiment, the hydrocarbon is heptane. In another embodiment, the anti-solvent is heptane and further contains other hydrocarbons.

The inventors found that the crystallinity and yield of the purified crystalline CCI-779 is affected by the acetone content, induction time, and anti-solvent addition. Specifically, highly crystalline purified CCI-779 was obtained in high yields with low levels of acetone, a long induction time, and a non-linear addition of the anti-solvent.

As used herein, the phrase "induction time" refers to the period of time between addition of the first solvent and the start of the addition of the anti-solvent. In one embodiment, the induction time is about 0.5 to about 5 hours. In yet another embodiment, the induction time is about 1 to 3 hours. However, the induction time is quite variable and depends on the amount of time required to obtain an acceptable content of the first solvent in the second solvent and amount of time required to adjust the nucleation time during measurement with the FBRM® instrument.

The term "non-linear" as used herein refers to the rate of the anti-solvent addition, whereby the rate varies with time. Desirably, the anti-solvent is initially slowly added to the second solvent and thereafter the rate of addition is increased over time. The inventors have found that if the initial addition of the anti-solvent is too fast, small-needle-like particles of CCI-779 with poor flow are formed as an oil, a fine, poorly crystalline material, or a fine, non-crystalline material, thereby indicating primary nucleation. A non-linear addition of the anti-solvent also results in the formation of crystalline purified CCI-779 with consistent morphology and size. In one embodiment, crystalline purified CCI-779 is prepared as rod-like crystalline particles. In another embodiment, the crystalline purified CCI-779 contains particles about 10 to about 100 µm in length.

The term "primary nucleation" as used herein refers to precipitation of CCI-779, whereby crystal particles of CCI-779 are not formed. This term differs from the crystallization of CCI-779, whereby crystalline CCI-779 is formed.

Desirably, the flow rate of the anti-solvent is normalized and expressed as a 1:1 ratio of the rate of anti-solvent addition (L/hr) to the amount of crude CCI-779 (kg). However, one of skill in the art would also readily be able to utilize a slower flow rate. Typically, the anti-solvent is initially added at a rate of about 2 L/hour/kg crude CCI-779. Thereafter, the anti-solvent addition rate is increased, desirably to about 3 L/hour/kg crude CCI-779. This increased anti-solvent addition rate can be maintained or thereafter increased to a faster addition, such as about 11 L/hour/kg crude CCI-779. In one embodiment, the anti-solvent is added over a period of about 120 to about 240 minutes. In another embodiment, the anti-solvent is added over a period of about 180 minutes. In a further embodiment, the anti-solvent is initially added at a rate of 1 L/hour/kg crude CCI-779, thereby increased to a rate of 3 L/hour/kg crude CCI-779 in the second hour, and finally increased to a rate of 11 L/hour/kg crude CCI-779 in the last 30 minutes.

The purified crystalline CCI-779 is collected using techniques known to those of skill in the art and include, without limitation, filtration, decanting, centrifugation, among others. Once collected, the purified crystalline CCI-779 is optionally washed, once or multiple times, with the anti-solvent, second solvent, or combination thereof. In one embodiment, the purified crystalline CCI-779 is washed with an ether and an anti-solvent. In another embodiment, the purified crystalline CCI-779 is washed with a diethyl ether and heptane solution. Once collected and optionally washed, the purified crystalline CCI-779 is dried using techniques known to those of skill in the art, and optionally micronized using the micronization techniques as described above for unpurified CCI-779. Typically, the purified crystallized CCI-779 prepared according to the present invention is micronized to prepare particles of less than about 30 µm.

The purified crystalline CCI-779 can also be further purified by repeating the steps of the process of the invention.

In one example, the present invention provides a process for purifying CCI-779 including (i) dissolving CCI-779 in a ketone; (ii) filtering the product of step (i); (iii) removing the ketone from the product of step (ii); (iv) dissolving the product of step (iii) in an ether; (v) measuring the content of the ketone in the product of step (iv), wherein if the ketone content is greater than 4 vol %, the ether is removed and steps (iv) and (v) are repeated; (vi) measuring the nucleation point of the product of step (iv) by focused beam reflectance measurement and adjusting the nucleation hold time until the chord count is greater than 1500 chords/second for 1 to 5 µm particles of the CCI-779; (vii) optionally adding pentanediol to the product of step (vi); (viii) adding an anti-solvent to the product of step (vii); and (ix) collecting purified crystalline CCI-779, wherein steps (i) to (ix) and/or steps (iv) to (ix) are optionally repeated with said purified CCI-779.

In another example, the present invention provides a process for purifying CCI-779 including (i) dissolving unpurified CCI-779 in acetone; (ii) filtering the solution of step (i); (iii) removing the acetone from the product of step (ii); (iv)

dissolving the product of step (iii) in diethylether; (v) measuring the content of the acetone in the product of step (iv), wherein if the acetone content is greater than 4 vol %, the diethylether is removed and steps (iv) and (v) are repeated; (vi) measuring the nucleation point in the product of step (iv) by focused beam reflectance measurement and adjusting the nucleation hold time until the chord count is greater than 1500 chords/second for 1 to 5 µm particles of the CCI-779; (vii) optionally adding pentanediol to the diethylether; (viii) adding heptane to the product of step (vii) over a period of 120 to 240 minutes; (ix) collecting purified CCI-779; and (x) drying purified CCI-779 under reduced pressures at a temperature of about 25 to about 50° C., wherein step (vii) is performed about 0.5 to about 5 hours after step (iv) and wherein steps (i) to (x) and/or (iv) to (ix) are optionally repeated with said purified CCI-779.

In a further example, the present invention provides a method for monitoring crystallization of CCI-779, including (i) dissolving unpurified CCI-779 in a first solvent; (ii) removing the first solvent from the product of (i); (iii) dissolving the product of step (ii) in a second solvent; (iv) measuring the content of the first solvent in the product of (iii), wherein if the content of the first solvent is greater than a predetermined solvent content, the second solvent is removed and steps (ii) and (ii) are repeated; (v) measuring the nucleation point of CCI-779 in the second solvent by focused beam reflectance measurement and adjusting the nucleation hold time until the chord count is the same or greater than a predetermined nucleation chord count.

B. Compositions Containing Purified Crystalline CCI-779

The present invention also provides compositions, preferably pharmaceutical compositions, containing purified crystalline CCI-779 alone or in combination with unpurified CCI-779. The compositions typically contain a pharmaceutically acceptable carrier, but can also contain other suitable components. Typically, the additional components are inert and do not interfere with the function of the required components of the compositions. The compositions of the present invention can thereby further include other adjuvants, syrups, elixirs, diluents, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, povidone, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl furamate, among others. In one embodiment, the lubricant is magnesium stearate.

Granulating agents can include, without limitation, silicon dioxide, starch, calcium carbonate, pectin, crospovidone, and polyplasdone, among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing CCI-779 to about 4 to about 6. In one embodiment, the pH of a solution containing CCI-779 is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used in the composition of the present invention include mannitol, calcium phosphate, pregelatinized starch, or sucrose.

C. Methods of Using Purified Crystalline CCI-779

The invention further provides methods of delivering purified CCI-779 to a patient, where the method includes administering purified CCI-779 according to the invention.

The dosage requirements of purified crystalline CCI-779 may vary based on the severity of the symptoms presented and the particular subject being treated. Treatment can be initiated with small dosages less than the optimum dose of purified crystalline CCI-779. Thereafter the dosage is increased until the optimum effect under the circumstances is reached. Precise dosages will be determined by the administering physician based on experience with the individual subject treated. In general, purified crystalline CCI-779 is most desirably administered at a concentration that will generally afford effective results without causing any unacceptable harmful or deleterious side effects. For example, an effective amount of purified crystalline CCI-779 is generally, e.g., about 0.1 to about 50 mg, about 10 mg to about 30 mg, or about 0.5 to about 2 mg.

Purified crystalline CCI-779 is therefore useful as an antineoplastic agent, and in particular, in treatment of sarcomas and carcinomas, astrocytomas, prostate cancer, breast cancer, colon cancer, small cell lung cancer, ovarian cancer, central nervous system cancer, melanoma, gliomas, glioblastoma, and adult T-cell leukemia/lymphoma. Purified crystalline CCI-779 is also useful treatment or inhibition of transplantation rejection such as kidney, heart, liver, lung, bone marrow, pancreas (islet cells), cornea, small bowel, and skin allografts, and heart valve xenografts; graft vs. host disease; autoimmune diseases such as lupus, rheumatoid arthritis, diabetes mellitus, myasthenia gravis, and multiple sclerosis; for treating diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; fungal infections; hyperproliferative vascular diseases such as restenosis, graft vascular atherosclerosis, cardiovascular disease, cerebral vascular disease, peripheral vascular disease such as coronary artery disease, cereberovascular disease, arteriosclerosis, atherosclerosis, nonatheromatous arteriosclerosis, or vascular wall damage from cellular events leading toward immune mediated vascular damage, stroke or multiinfarct dementia.

Purified crystalline CCI-779 can be formulated in any form suitable for the desired route of delivery using a pharmaceutically effective amount of purified crystalline CCI-779. For example, purified crystalline CCI-779 can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

For example, purified crystalline CCI-779 may be formulated for administration orally in such forms as tablets, capsules, microcapsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like. The preferred pharmaceutical compositions from the standpoint of ease of preparation and administration are solid compositions, particularly tablets and hard-filled or liquid-filled capsules.

Purified crystalline CCI-779 may also be administered parenterally or intraperitoneally. Solutions or suspensions of purified crystalline CCI-779 as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms. Typically, such sterile injectable solutions or suspensions contain from about 0.05 to 5% suspending agent in an isotonic medium. Such pharmaceutical preparations may contain, for example, from about 25 to about 90% of the active ingredient in combination with the carrier, more usually between about 5% and 60% by weight.

In another embodiment, purified crystalline CCI-779 is delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile, stable under conditions of manufacture and storage, and free of the contaminating action of microorganisms such as bacteria and fungi.

The carrier can be a solvent or dispersion medium containing, for example, water, ethanol (e.g., glycerol, propylene glycol and liquid polyethylene glycol), oils, and mixtures thereof. Preferably the liquid carrier is water. In one embodiment, the oil is vegetable oil. Optionally, the liquid carrier contains a suspending agent. In another embodiment, the liquid carrier is an isotonic medium and contains 0.05 to about 5% suspending agent.

In a further embodiment, purified crystalline CCI-779 is delivered rectally in the form of a conventional suppository.

In another embodiment, purified crystalline CCI-779 is delivered vaginally in the form of a conventional suppository, cream, gel, ring, or coated intrauterine device (IUD).

In yet another embodiment, purified crystalline CCI-779 is delivered intranasally or intrabronchially in the form of an aerosol.

In a further embodiment, purified crystalline CCI-779 is delivered transdermally or by sustained release through the use of a transdermal patch containing purified crystalline CCI-779 and an optional carrier that is inert to purified crystalline CCI-779, is nontoxic to the skin, and allows for delivery of purified crystalline CCI-779 for systemic absorption into the blood stream. Such a carrier can be a cream, ointment, paste, gel, or occlusive device. The creams and ointments can be viscous liquid or semisolid emulsions. Pastes include absorptive powders dispersed in petroleum or hydrophilic petroleum. Further, a variety of occlusive devices can be utilized to release purified crystalline CCI-779 into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., purified crystalline CCI-779, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, purified crystalline CCI-779 can be formulated as described herein. See, U.S. Pat. Nos. 3,845,770; 3,916,899; 3,536,809; 3,598,123; and 4,008,719.

Purified crystalline CCI-779 typically formed into a suitable dosing unit for delivery to a patient. Suitable dosing units include oral dosing units, such as a directly compressible tablets, capsules, powders, suspensions, microcapsules, dispersible powders, granules, suspensions, syrups, elixirs, and aerosols. These dosing units are readily prepared using the methods described herein and those known to those of skill in the art.

In one embodiment, when administered orally, the capsules utilized in the present invention include hydroxypropyl methylcellulose, hypromellose capsule, or a hard shell gelatin capsule. The tablets or caplets of the present invention that contain purified crystalline CCI-779 are optionally film-coated. Suitable film-coatings are known to those of skill in the art. For example, the film-coating can be selected from among polymers such as hydroxypropylmethylcellulose, ethyl cellulose, polyvinyl alcohol, and combinations thereof.

A pharmaceutically effective amount of purified crystalline CCI-779 can vary depending on the other components of the composition being delivered, mode of delivery, severity of the condition being treated, the patient's agent and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

When utilized for treating neoplastic disease, carcinomas, and adenocarcinomas, purified crystalline CCI-779 can be administered in conjunction with one or more chemotherapeutic agents which can readily be selected by one of skill in the art.

D. Kits Containing Purified CCI-779

The present invention also provides kits or packages containing purified crystalline CCI-779. Kits of the present invention can include purified crystalline CCI-779 or in combination with less pure forms and a carrier suitable for administration to a mammalian subject as discussed above.

Preferably, the daily dosage of purified crystalline CCI-779 remains fixed in each particular phase in which it is delivered. The kit can further contain instructions for administering purified crystalline CCI-779.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

General Process for Preparing Purified Crystalline CCI-779

This example provides a process for preparing purified, crystalline CCI-779 from crude CCI-779.

Crude CCI-779 (200 g, 19.4 mol) was dissolved in acetone (1.61 L) in a 3 L jacketed reactor (Chemglass) equipped with an external heater/chiller, vacuum distillation apparatus, 1 baffle housing the reactor temperature probe, overhead stirrer with a 4 pitched-blade turbine impeller. The reactor was also fitted with Lasentec® D600L focused beam reflectance measurement system (FBRM® system) using a 18" hastealloy probe (0.7" OD) fitted with a sapphire window (from Mettler Toledo Inc). The solution was then clarified through filtration using a 0.45 µm polypropylene filter element. Acetone was removed from the resulting solution under vacuum to obtain a foam. Diethyl ether (1.27 L) was added and the distillation continued until the level of acetone in the resulting solution was less than 4 vol %. The solution was stirred until a slurry was obtained.

The nucleation process was monitored by using the FBRM® instrument and the hold time was adjusted to achieve stable nucleation until the chord count was greater than about 1500 chords/second for particles about 1 to about 5 µm. The slurry was stirred for additional time until the chord count for 1 to 5 µm particles indicated the end of the spontaneous nucleation event. The slurry was treated with 2-methyl-2,4-pentanediol (0.13 L) at 20-25° C. to scavenge the residual phenylboronic acid. Heptane (3.14 L) was added to the slurry using a programmable piston pump (Stepdos) which was used for controlled anti-solvent addition at a segmented non-linear addition rate. Upon dilution with heptane by controlled addition over 3 hours, the slurry was filtered to give large white crystals of purified crystalline CCI-779 (mp onset=169° C.) in 84% yield, with total impurities of 1.25%, where 0.54% of the impurities were oxidative impurities.

Example 2

Preparation of Purified Crystalline CCI-779 Using Slower Filtration

Purified crystalline CCI-779 was prepared using the description provided in Example 1 except that the CCI-779 solution in acetone was filtered using a medium grit fritted glass funnel (75 mm ID). The filtration was slow and necessitated the use of 2 funnels in parallel. The total time required for the filtration was 2.1 hours.

The acetone was then removed as described in Example 1. The increased viscosity of the amorphous CCI-779 resulted in the agitator slowing down. The amorphous CCI-779 was held overnight under vacuum with the agitator switched off.

Following the addition of diethyl ether as described in Example 1, in which dissolution took about 11 minutes, nucleation of the CCI-779 was monitored. A sample of the solution was then withdrawn for acetone content analysis and was determined to be about 3.2 vol % acetone. The induction time for the appearance of nuclei was 54 minutes (see FIG. 1).

Following nucleation, the batch was aged for 34 minutes as indicated by the FBRM® instrument to obtain stabilization of the chord count. The pentanediol and heptane were added as described in Example 1. The isolated purified crystalline CCI-779 was washed and dried at 40 EC under vacuum for 48 hours. A yield of 176.3 g of purified crystalline CCI-779 was obtained (87.6%). See Table 1 for the HPLC data for the purified CCI-779 obtained immediately after crystallization and samples tested after 2 weeks and 1 month at varying conditions.

TABLE 1

| Storage | Time Point | HPLC Strength (%) |
|---|---|---|
| | Initial | 101.09 |
| 5° C. | 2 Weeks | 101.09 |
| | 1 Month | 97.42 |
| 25° C./60% RH | 2 Weeks | 101.07 |
| | 1 Month | 97.87 |

Example 3

Preparation of Purified Crystalline CCI-779 with Faster Filtration

This example was performed using the same protocol as described in Example 2. However, filtration of the crude CCI-779 solution in acetone was completed in 30 minutes by using a medium grit fritted funnel. Following distillation of the acetone, the batch was held as an amorphous foam/oil for 2 hours under reduced pressures. Diethyl ether was then added to the foam/oil and the diethyl ether solution was evaluated for acetone content (8.5 vol %). The diethylether (containing acetone) was then removed by distillation to obtain an amorphous foam. This foam was maintained under reduced pressures for 30 minutes and diethyl ether again added. The diethylether was again monitored for acetone contact and determined to be less than 3.6 vol % acetone. The crystallization was the continued as in Example 2. The induction time for nucleation, i.e., the time required to obtain a chord count for particles of about 1 to about 5 µm particles of greater than about 1500 chords/s was 26 minutes. Following the nucleation, the slurry was stirred for additional time to ensure stabilization of the nucleation. Following isolation and drying as outlined above, a final yield of 175.1 g of purified crystalline CCI-779 was obtained (87.3%). See Table 2, for the HPLC data for the purified crystalline CCI-779 obtained immediately after crystallization and samples tested after 2 weeks and 1 month at varying conditions.

TABLE 2

| Storage | Time Point | HPLC Strength (%) |
|---|---|---|
| | Initial | 100.45 |
| 5° C. | 2 Weeks | 100.45 |
| | 1 Month | 97.55 |
| 25° C./60% RH | 2 Weeks | 101.30 |
| | 1 Month | 97.81 |

Example 4

Preparation of Purified Crystalline CCI-779 with Controlled Heptane Addition

This example provides a semi-batch crystallization process to improve crystallinity. The process is carried out in a reactor with accurate temperature control, overhead stirring and ability to carry out controlled solvent feed. For optimal control, the reactor is fitted with a Lasentec® FBRM® probe measuring chord lengths in the 1-500 µm range using "fines" electronics.

Acetone (5.7 L) is added to crude CCI-779 (1 kg). The acetone solution is stirred at high revolutions per minute at 22° C. (jacket) until a clear solution is obtained as monitored by the Lasentec® system particle count. The clear solution is filtered through a 0.45 µm in-line filter. The filter is washed with acetone (2 L) and the acetone wash added to the filtered solution. The acetone of the filtered solution is removed under reduced pressures by distillation at a temperature of about 5-20° C. until a foam is obtained. The foam is maintained under reduced pressures for about 2 hours.

Diethyl ether (3.4 L) is added to the dried foam and the solution stirred at 22° C. After 10 minutes, the solid is collected by filtration and the diethylether solution is monitored by gas chromatography (GC) to monitor the amount of acetone remaining in the diethylether. The diethylether wash is repeated if the acetone content is greater than about 3 vol % of the diethylether.

The diethyl ether washed sample is again combined with diethyl ether, is mixed for 30 minutes, and the particle count is measured using the FBRM® instrument. After verification that the particle count is greater than 1500 chords/second for 1-5 µm range, the slurry is mixed for an additional 30 minutes. A visual inspection is also performed to confirm that a slurry is present.

A pentanediol solution (0.7 L pentanediol in 0.4 L diethyl ether) is then added to the diethyl ether slurry over a period of at least 15 minutes. The solution is mixed for 60 minutes at a temperature of about 22° C. or until the Lasentec® system particle count is stable. Heptane (10.7 L) is added to the solution while maintaining a temperature of about 22° C. over a period of about 150 minutes using the following profile:

1. Add the first 2 L in first 60 minutes;
2. Add 3 L in second 60 minutes; and
3. Add 5.7 L in next 30 minutes.

The slurry is then mixed for 4 hours at a temperature of about 22° C., the slurry filter, and the solid washed 3 times with a solvent mixture of ether/heptanes (0.9/4.8 L). The solid is dried at a temperature of about 40° C. under reduced pressures.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A purified crystalline form of CCI-779 which retains greater than 97% strength over a period of at least about 3 months and having:
   (i) a differential scanning calorimetry thermogram having an endotherm peak of greater than about 165° C.; or
   (ii) an X-ray diffraction peak pattern having peaks at 2θ of 7.7, 9.0, 11.4, 12.6, 13.3, 15.0, 15.4, 16.2, 66.5, 34.8, 43.7, 31.4, and 58.

2. The crystalline form according to claim 1, which comprises less than 0.1% wt/wt of phenylboronic acid.

3. The crystalline form according to claim 1, which comprises less than 0.6% wt/wt of oxidative impurities.

4. The crystalline form according to claim 1, which comprises less than about 0.3% wt/wt of acetone.

5. A purified crystalline form of CCI-779 according to claim 1, having:
   (i) a differential scanning calorimetry thermogram having an endotherm peak greater than about 165° C.;
   (ii) an X-ray diffraction peak pattern having peaks at 2θ of 7.7, 9.0, 11.4, 12.6, 13.3, 15.0, 15.4, 16.2, 66.5, 34.8, 43.7, 31.4, and 58.

6. A process for purifying CCI-779 comprising:
   (i) dissolving CCI-779 in a ketone;
   (ii) filtering the product of step (i);
   (iii) removing said ketone from the product of step (ii);
   (iv) dissolving the product of step (iii) in an ether;
   (v) measuring the content of said ketone in the product of step (iv);
   wherein if the ketone content is greater than 4 vol %, said ether is removed and steps (iv) and (v) are repeated;
   (vi) measuring the nucleation point of the product of step (iv) by focused beam reflectance measurement and adjusting the nucleation hold time until the chord count is greater than 1500 chords/second for 1 to 5 µm particles of said CCI-779;
   (vii) optionally adding pentanediol to the product of step (vi);
   (viii) adding an anti-solvent to the product of step (vii); and
   (ix) collecting purified CCI-779;
   wherein steps (i) to (ix) or step (iv) to (ix) are optionally repeated with said purified CCI-779 and
   wherein purified CCI-779 retains greater than 97% strength over a period of at least about 3 months and has:
   (i) a differential scanning calorimetry thermogram having an endotherm peak of greater than about 165° C.; or
   (ii) an X-ray diffraction peak pattern having peaks at 2θ of 7.7, 9.0, 11.4, 12.6. 13.3, 15.0, 15.4, 16.2, 66.5, 34.8, 43.7, 31.4, and 58.

7. The process according to claim 6, wherein the product of step (iii) is amorphous.

8. The process according to claim 6, wherein said ketone is acetone.

9. The process according to claim 6, wherein said ether is similar in polarity to diethyl ether.

10. The process according to claim 9, wherein said ether is diethyl ether.

11. The process according to claim 6, wherein said anti-solvent is heptane.

12. The process according to claim 11, wherein said anti-solvent further comprises other hydrocarbons.

13. The process according to claim 6, wherein step (vii) is performed about 0.5 to about 5 hours after step (iv).

14. The process according to claim 13, wherein step (vii) is performed about 1 to 3 hours after step (iv).

15. The process according to claim 6, wherein crystallization of purified CCI-779 begins in step (iv), step (v), (vi), or between steps (iv) and (vi).

16. The process according to claim 6, wherein said anti-solvent is added non-linearly.

17. The process according to claim 16, wherein the initial rate of addition of said anti-solvent is slow.

18. The process according to claim 17, wherein the rate of addition of said anti-solvent is increased over time.

19. The process according to claim 6, wherein said anti-solvent is added over a period of about 120 to about 240 minutes.

20. The process according to claim 19, wherein said anti-solvent is added over a period of about 180 minutes.

21. The process according to claim 6, wherein step (vii) is optionally performed about 0.5 to about 5 hours after step (iv).

22. The process according to claim 6, wherein said purified CCI-779 is washed with an ether and an anti-solvent.

23. The process according to claim 6, wherein said purified CCI-779 is dried.

24. The process according to claim 6, further comprising the step of drying the purified CCI-779 under reduced pressures at a temperature of about 25 to about 50° C., and wherein the steps are optionally repeated with said purified CCI-779.

25. A method for monitoring crystallization of CCI-779, comprising:
  (i) dissolving unpurified CCI-779 in a first solvent;
  (ii) removing the first solvent from the product of (i);
  (iii) dissolving the product of step (ii) in a second solvent;
  (iv) measuring the content of said first solvent in the product of (iii);
    wherein if the content of the first solvent is greater than a predetermined solvent content, said second solvent is removed and steps (ii) and (ii) are repeated;
  (v) measuring the nucleation point of CCI-779 in said second solvent by focused beam reflectance measurement and adjusting the nucleation hold time until the chord count is the same or greater than a predetermined nucleation chord count.

26. A kit comprising (i) purified crystalline CCI-779 of claim 1; and (ii) a carrier suitable for administration to a mammalian subject.

27. A pharmaceutical composition comprising purified crystalline CCI-779 of claim 1, and one or more of:
  (i) a metal chelator;
  (ii) a pH adjuster;
  (iii) a surfactant;
  (iv) at least one filler;
  (v) a binder;
  (vi) a disintegrant; and
  (vii) a lubricant.

28. A method for treating central nervous system cancer, leukemia, breast cancer, prostate cancer, melanoma, gliomas, and glioblastoma comprising administering the purified crystalline form of CCI-779 of claim 1 to a mammalian subject in need thereof.

* * * * *